(12) United States Patent
Karpowicz et al.

(10) Patent No.: US 8,771,259 B2
(45) Date of Patent: *Jul. 8, 2014

(54) SYSTEM FOR TREATING A WOUND WITH SUCTION AND METHOD OF DETECTING A LOSS OF SUCTION

(75) Inventors: John Karpowicz, Chester Springs, PA (US); Christopher L. Radl, Malvern, PA (US); Kevin P. Klocek, Wynnewood, PA (US); John R. Boehringer, Wynnewood, PA (US); Derek Norton, Collegeville, PA (US)

(73) Assignee: Boehringer Technologies, L.P., Phoenixville, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/556,839

(22) Filed: Jul. 24, 2012

(65) Prior Publication Data

US 2012/0289915 A1 Nov. 15, 2012

Related U.S. Application Data

(60) Continuation of application No. 12/207,241, filed on Sep. 9, 2008, now Pat. No. 8,246,607, which is a division of application No. 11/268,212, filed on Nov. 7, 2005, now Pat. No. 7,438,705.

(60) Provisional application No. 60/699,218, filed on Jul. 14, 2005.

(51) Int. Cl.
*A61M 27/00* (2006.01)
*A61M 1/00* (2006.01)

(52) U.S. Cl.
CPC ....... *A61M 27/00* (2013.01); *A61M 2001/0029* (2013.01)

USPC .......................................... 604/543; 604/313

(58) Field of Classification Search
CPC ..................... A61M 27/00; A61M 2001/0029
USPC .......................... 604/313, 315–316, 541, 543
See application file for complete search history.

(56) References Cited

U.S. PATENT DOCUMENTS

| | | |
|---|---|---|
| 3,042,041 A | 7/1962 | Jascalevich |
| 3,397,648 A | 8/1968 | Henderson |

(Continued)

FOREIGN PATENT DOCUMENTS

| | | |
|---|---|---|
| EP | 0853950 | 7/1998 |
| EP | 0777504 | 10/1998 |

(Continued)

OTHER PUBLICATIONS

The Engineerig ToolBox: Positive Displacement Pumps, literature, website: http://www.engineeringtoolbox.com, Sep. 15, 2008.

(Continued)

*Primary Examiner* — Melanie Hand
*Assistant Examiner* — Paula Craig
(74) *Attorney, Agent, or Firm* — Caesar, Rivise, Bernstein, Cohen & Pokotilow, Ltd.

(57) ABSTRACT

A system for applying suction to a wound is provided, including a suction source for providing suction to a conduit operatively associated with the wound to communicate suction to the wound, a vent in fluid communication with the conduit to provide a reference airflow into the conduit when the system is in operation, such that a loss of suction at the wound is indicated by deviation from the reference airflow, and a waste collector canister between the wound and the suction source for collecting liquids aspirated from the wound, wherein the canister includes one or more disks containing gelling agent.

1 Claim, 8 Drawing Sheets

(56) References Cited

U.S. PATENT DOCUMENTS

| | | | |
|---|---|---|---|
| 3,568,675 A | 3/1971 | Harvey | |
| 3,599,639 A | 8/1971 | Spotz | |
| RE28,405 E | 5/1975 | Sullerud | |
| 3,889,677 A | 6/1975 | Nehring | |
| 4,180,074 A | 12/1979 | Murry et al. | |
| 4,231,375 A | 11/1980 | Boehringer et al. | |
| 4,257,437 A | 3/1981 | Pearson | |
| 4,341,235 A | 7/1982 | Nord | |
| 4,385,630 A | 5/1983 | Gilcher et al. | |
| 4,453,937 A | 6/1984 | Kurtz et al. | |
| 4,468,219 A * | 8/1984 | George et al. | 604/66 |
| 4,569,674 A * | 2/1986 | Phillips et al. | 604/119 |
| 4,655,754 A * | 4/1987 | Richmond et al. | 604/323 |
| 4,664,601 A * | 5/1987 | Uchida et al. | 417/27 |
| 4,706,687 A * | 11/1987 | Rogers et al. | 600/565 |
| 4,710,165 A | 12/1987 | McNeil | |
| 4,735,606 A * | 4/1988 | Davison | 604/28 |
| 4,738,671 A | 4/1988 | Elliott et al. | |
| 4,797,666 A | 1/1989 | Baxter et al. | |
| 4,798,583 A * | 1/1989 | Beck et al. | 604/48 |
| 4,930,997 A | 6/1990 | Bennett | |
| 4,933,843 A * | 6/1990 | Scheller et al. | 604/22 |
| 4,969,880 A | 11/1990 | Zamierowski | |
| 4,971,034 A | 11/1990 | Doi et al. | |
| 5,047,072 A | 9/1991 | Wertz et al. | |
| 5,092,858 A | 3/1992 | Benson et al. | |
| 5,094,105 A | 3/1992 | Emmert, Jr. et al. | |
| 5,380,308 A | 1/1995 | Gunya et al. | |
| 5,429,601 A * | 7/1995 | Conley et al. | 604/65 |
| 5,549,584 A | 8/1996 | Gross | |
| 5,630,807 A * | 5/1997 | Joffe | 604/315 |
| 5,636,643 A | 6/1997 | Argenta et al. | |
| 5,656,027 A * | 8/1997 | Ellingboe | 604/541 |
| 5,738,656 A * | 4/1998 | Wagner | 604/119 |
| 5,836,909 A | 11/1998 | Cosmescu | |
| 5,941,859 A | 8/1999 | Lerman | |
| 6,045,541 A | 4/2000 | Matsumoto et al. | |
| 6,071,267 A | 6/2000 | Zamierowski | |
| 6,142,982 A | 11/2000 | Hunt et al. | |
| 6,159,180 A | 12/2000 | Kriesel et al. | |
| 6,458,109 B1 | 10/2002 | Henley et al. | |
| 6,533,757 B1 | 3/2003 | Lampropoulos et al. | |
| 6,557,704 B1 | 5/2003 | Randolph | |
| 6,599,277 B2 | 7/2003 | Neubert | |
| 6,648,862 B2 | 11/2003 | Watson | |
| 6,685,681 B2 | 2/2004 | Lockwood et al. | |
| 6,695,823 B1 | 2/2004 | Lina et al. | |
| 6,755,807 B2 | 6/2004 | Risk, Jr. et al. | |
| 6,764,462 B2 | 7/2004 | Risk, Jr. et al. | |
| 6,824,533 B2 | 11/2004 | Risk, Jr. et al. | |
| 6,929,619 B2 | 8/2005 | Fago et al. | |
| 6,960,190 B2 | 11/2005 | Stinson | |
| 6,979,324 B2 | 12/2005 | Bybordi et al. | |
| 7,004,915 B2 | 2/2006 | Boynton et al. | |
| 7,122,018 B2 * | 10/2006 | Stenzler et al. | 604/23 |
| 7,128,735 B2 | 10/2006 | Weston | |
| 7,144,390 B1 | 12/2006 | Hannigan et al. | |
| 7,195,624 B2 | 3/2007 | Lockwood et al. | |
| 7,438,705 B2 | 10/2008 | Karpowicz et al. | |
| 7,553,306 B1 | 6/2009 | Hunt et al. | |
| 7,708,724 B2 | 5/2010 | Weston | |
| 7,857,806 B2 * | 12/2010 | Karpowicz et al. | 604/540 |
| 8,246,607 B2 | 8/2012 | Karpowicz et al. | |
| 2002/0138051 A1 | 9/2002 | Hole et al. | |
| 2002/0161317 A1 | 10/2002 | Risk et al. | |
| 2002/0188279 A1 | 12/2002 | Waddell et al. | |
| 2002/0198503 A1 | 12/2002 | Risk, Jr. et al. | |
| 2002/0198504 A1 | 12/2002 | Risk, Jr. et al. | |
| 2003/0014022 A1 | 1/2003 | Lockwood et al. | |
| 2003/0040687 A1 | 2/2003 | Boynton et al. | |
| 2003/0093041 A1 | 5/2003 | Risk, Jr. et al. | |
| 2003/0098854 A1 | 5/2003 | Laliberte et al. | |
| 2004/0006319 A1 | 1/2004 | Lina et al. | |
| 2004/0054338 A1 | 3/2004 | Bybordi et al. | |
| 2004/0064132 A1 | 4/2004 | Boehringer et al. | |
| 2004/0208756 A1 | 10/2004 | Adahan | |
| 2005/0004534 A1 | 1/2005 | Lockwood et al. | |
| 2005/0124966 A1 | 6/2005 | Karpowicz et al. | |
| 2005/0209574 A1 | 9/2005 | Boehringer et al. | |
| 2005/0215961 A1 | 9/2005 | Romano et al. | |
| 2005/0222544 A1 | 10/2005 | Weston | |
| 2005/0228329 A1 | 10/2005 | Boehringer et al. | |
| 2005/0287007 A1 | 12/2005 | Leonhard | |
| 2006/0025727 A1 | 2/2006 | Boehringer et al. | |
| 2006/0027267 A1 | 2/2006 | Fritze | |
| 2006/0036221 A1 | 2/2006 | Watson, Jr. | |
| 2006/0100586 A1 * | 5/2006 | Karpowicz et al. | 604/180 |
| 2006/0129137 A1 | 6/2006 | Lockwood et al. | |
| 2006/0196505 A1 | 9/2006 | Izuchukwu | |
| 2007/0016152 A1 | 1/2007 | Karpowicz et al. | |
| 2007/0032754 A1 | 2/2007 | Walsh | |
| 2007/0032755 A1 | 2/2007 | Walsh | |
| 2007/0167927 A1 | 7/2007 | Hunt et al. | |
| 2007/0219532 A1 * | 9/2007 | Karpowicz et al. | 604/540 |
| 2008/0071214 A1 | 3/2008 | Locke et al. | |
| 2008/0071216 A1 | 3/2008 | Locke et al. | |
| 2008/0071234 A1 | 3/2008 | Kelch et al. | |
| 2008/0071235 A1 | 3/2008 | Locke et al. | |
| 2008/0077078 A1 | 3/2008 | Locke et al. | |
| 2008/0228526 A1 | 9/2008 | Locke et al. | |
| 2009/0043268 A1 | 2/2009 | Eddy et al. | |
| 2009/0137973 A1 | 5/2009 | Karpowicz et al. | |
| 2009/0264837 A1 | 10/2009 | Adahan | |
| 2011/0077605 A1 * | 3/2011 | Karpowicz et al. | 604/318 |

FOREIGN PATENT DOCUMENTS

| | | |
|---|---|---|
| WO | 9605873 | 2/1996 |
| WO | 9718007 | 5/1997 |
| WO | 0021586 | 4/2000 |
| WO | 0134223 | 5/2001 |
| WO | 0137922 | 5/2001 |
| WO | 03016719 | 2/2003 |
| WO | 03057070 | 7/2003 |
| WO | 2007013049 | 2/2007 |
| WO | 2008039223 | 4/2008 |
| WO | 2008039314 | 4/2008 |

OTHER PUBLICATIONS

Blue Sky Medical, Vista Versatile 1 Portable, 20 sheets, website: http://www.blueskymedical.com, Feb. 29, 2008.

Miller, et al., BioMechanics, "Negative Pressure Wound Therapy Options Promote Patient Care," article, Sep. 2005.

V.A.C. Instill, Dual Therapies, "One Advanced Wound Healing system," KCI brochure.

KCI, V.A.C., Instill, Recommended Guidelines, brochure, Aug. 2004.

KCI, V.A.C. Therapy Wound Reference, No. 4 series, Orthopedic Trauma Wounds, brochure, 2005, 2006.

KCI, V.A.C. Therapy Clinical Guidelines, manual, Jul. 2007.

* cited by examiner

SYSTEM FOR TREATING A WOUND WITH SUCTION AND METHOD OF DETECTING A LOSS OF SUCTION

CROSS-REFERENCES TO RELATED APPLICATIONS

This application is a Continuation Application of utility U.S. application Ser. No. 12/207,241, entitled System for Treating a Wound with Suction and Method Detecting Loss of Suction, filed Sep. 9, 2008, now U.S. Pat. No. 8,246,607, which is a Divisional Application of utility U.S. application Ser. No. 11/268,212, entitled System for Treating a Wound with Suction and Method Detecting Loss of Suction, filed Nov. 7, 2005, now U.S. Pat. No. 7,438,705, which claims priority to provisional U.S. Application Ser. No. 60/699,218, entitled Apparatus and System for Suction-Assisted Wound Healing, filed Jul. 14, 2005, the complete disclosures of which are fully incorporated by reference herein.

FIELD OF THE INVENTION

The invention is related to the general field of wound treatment, and to the more specific field of devices for wound drainage and treatment with suction.

BACKGROUND OF THE INVENTION

It is well known to treat wounds by applying suction under airtight wound covers. The suction can be used to aspirate wound exudate and other liquids from the wound and/or the wound packing materials, and suction can be applied as a healing modality for its well known antiseptic and tissue regeneration effects.

A primary concern in using suction assisted wound therapy is maintaining suction pressure at the wound. It is increasingly recognized that once suction wound dressings are applied, the suction should be maintained at certain levels. Loss of suction to the wound can result if leaks or blockages occur in the system.

Leaks can occur through breach of the airtight seals surrounding the wound. The earliest devices merely ran a tube under the edge of a wound cover and applied an adhesive or paste around the tube and cover to maintain an airtight seal. The other end of the tube was connectable to a waste collection reservoir and suction regulator of a hospital suction system, and the pressure selected at the regulator was assumed to be the approximate pressure communicated to the wound area under the cover. The test for leakage was visual observance of the cover contracting and the absence of whistling noise when negative pressure was applied. See, e.g., M. E. Chariker, et al, "Effective Management of Incisional and Cutaneous Fistulae with Closed Suction Wound Drainage", *Contemporary Surgery*, vol. 34, June 1989, pages 59-63. This initial check for an airtight seal did not, however, provide any warning if the system developed a leak or if blockage occurred in the collection circuit after hours of use.

The adhesive seal around the suction tube or other tubes which run under the edge of the wound cover in these prior wound dressings is vulnerable to cracking and breaching the airtight seal, creating air leakage into the cover. Improvements have been made to suction wound therapy devices to reduce the likelihood of leakage. For example, U.S. application Ser. No. 11/181,128, filed Jul. 14, 2005 and commonly assigned with this application, discloses a tube attachment patch to allow the suction tube to be terminated outside of the primary cover and thus reduce the risk of breaking the adhesive seal to the skin. While these newer tube attachment devices provide more seal integrity, there is still the potential for breach of the airtight seals due to patient movement in bed.

Blockage of suction to the wound can occur for several reasons. A waste collector for wound exudate is usually positioned somewhere in the suction line between the wound and the suction source. Waste collectors incorporate shut-off mechanisms that will shut off suction to the wound when the collector is overfilled. Another potential blockage is kinking or crimping of the suction line itself. Blockage due to debris from the wound and clotting is also a concern. The suction source may also be inadvertently turned off, a line may be inadvertently clamped, or the suction regulator may be misadjusted after the dressing is applied. Since suction wound dressings are intended to last for long periods without changing, usually 24 hours or greater, a leak or blockage could develop unnoticed and not be detected for a duration sufficient to negate the beneficial healing effect of suction as well as increase the risk of infection. There are currently devices to sense when a waste collector canister is filled and provide a warning signal to empty it. None of the devices, however, provides a comprehensive and reliable monitoring of system operation, nor cover the full range of fault possibilities with leakage or blockage.

In their efforts to improve over these prior art devices, the present inventors considered several design objectives for a suction wound dressing monitoring system; including the impracticality of locating expensive pressure transducers in any of the system components that should be single-use disposable items due to contamination by body fluids. The designers considered that the same basic system should preferably be effective in detecting and indicating both leaks and system blockage, and that the detection of leaks or blockage should preferably be effective regardless of where the leak or blockage occurs in the system. They considered that the system should preferably provide clear visual indication of both normal and abnormal operation, and could usefully provide aural indication and auto-recording of abnormalities. They also considered that the suction monitoring capability should be easily convertible from use with a stationary suction system, as typically found in hospital care rooms, to use with a portable suction pump.

These and other advantages and aspects of the invention will become apparent upon reading the detailed description and drawings that follow.

BRIEF SUMMARY OF THE INVENTION

The invention provides a system for applying suction to a wound in which a reference airflow rate is used for monitoring system operation. The basic components of a wound treatment system using suction include an airtight wound dressing, a suction conduit having one end operatively associated with the wound dressing to communicate suction to the wound, and an opposite end operatively connected with a source of suction, which may be a stationary source such as hospital wall suction or may be a portable pump. The invention provides a reference airflow rate (or "controlled leak") to the suction source when the system is in operation, such that deviation from the reference airflow can be monitored as an indication of a change in operation.

A wide variety of flow rate monitoring instruments can be used to display normal operation and detect deviation from the reference airflow, and several are depicted or described herein. In a stationary source configuration using a distributed hospital wall suction system, or a limited mobility suction pump using wall receptacle electrical power, a preferred wound monitoring instrument includes a flow meter that provides a visual indicator of normal and abnormal airflow rates, and may produce or trigger warning signals indicating abnormal conditions. In a portable battery-powered pump configuration, the preferred use of a positive displacement pump in which flow rate is proportional to motor rpm allows the airflow rate of the system to be indicated indirectly by the motor speed or pump speed. An algorithm may be used to correct motor and pump speed to flow for compressibility effect. Thus a motor speed indicator or tachometer may be the preferred monitoring instrument. However, in any of the vacuum source configurations, other flow rate monitoring instruments could be used, such as, but not limited to, target meters, rotometers, turbine meters, mass flow meters, differential pressure (Dp) cells and hot wire anemometers.

Although the term "airflow" herein for consistency, it should be apparent that it is not limited to the composition of ambient air. It is common in medical settings to alter the composition of airflow to a wound, such as by increased oxygen or therapeutic aerosols or other beneficial medications. The flow of any of these mixed gases or aerosol suspensions should be considered airflow for purpose of this description.

In a preferred embodiment, a calibrated vent in the suction conduit near the wound dressing establishes the reference airflow. Preferably the vent is located in the tube just outside of the wound cover. The vent may be an aperture in the tube sealed with a porous material having specific flow rate characteristics. The reference flow rate may be in a preferred range of 50-300 cc per minute. Higher flows such as 1000 cc/min are possible, but practical limitations on the capacity of the suction source as well as the magnitude of a leak in the dressing suggest that is preferable to use a flow below 1000 cc per minute.

By locating the vent in the conduit close to the wound, the reference airflow also serves to purge the conduit of fluids. The purging effect minimizes the likelihood of reflux of contaminated fluid back into the wound, and the risk of infection attendant to such reflux. Since the fluid does not reside in the conduit for an extended time, the purge effect also reduces the likelihood of blood clotting in the line.

The system may further include a waste collector, disposed in the suction line between the wound dressing and the source of suction, for collecting fluids aspirated from the wound. The preferred collector is an upright transparent plastic canister with fill level markings on the outside surface. The canister may be prevented from overfilling by a hydrophobic membrane filter at the top of the canister that shuts off the airflow when the canister is full. The liquids aspirated from the wound may be turned into a gel, for ease of disposal and to prevent spilling, by a gelling agent in the disposable canister. To keep the waste in the canister level, the gelling agent is preferably provided in stacked disks. The canister has an inlet connector for the suction tube from the wound dressing, and an outlet connector for connecting to a portable pump or to a flow monitoring instrument for use with stationary or hospital wall suction. The outlet connector is preferably a proprietary (non-standard) connector that will not connect directly to the standard appliance fitting of a stationary suction system, to prevent anyone from mistakenly connecting directly to the suction system.

The invention also includes the method of using a reference airflow to indicate normal operation of a suction wound therapy system, and deviation from the reference airflow to indicate leaks or blockage in the system, using the various apparatus described hereafter.

DETAILED DESCRIPTION OF THE INVENTION

Figure 1:
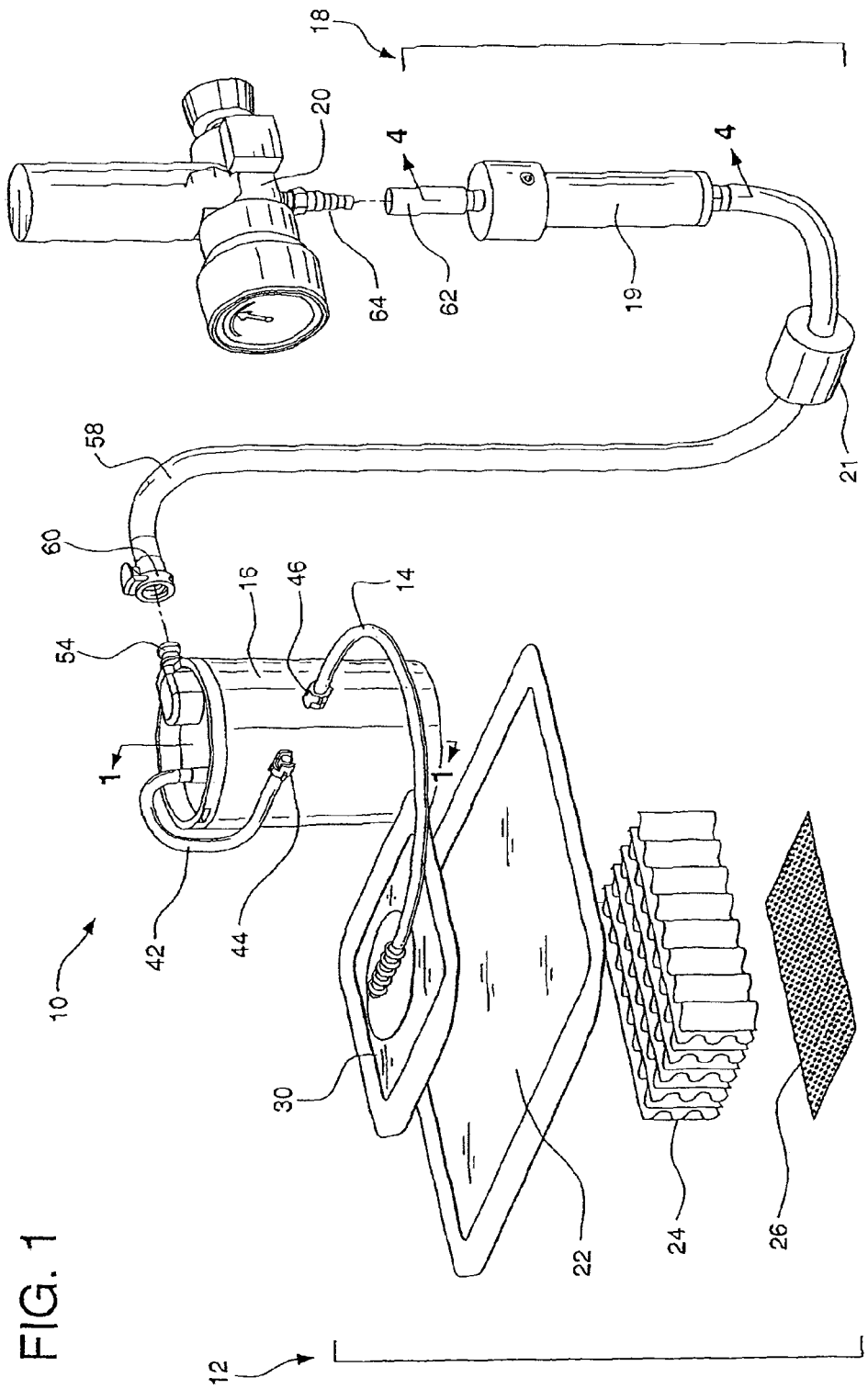
FIG. 1 is an exploded prospective view of a preferred embodiment of a system for suction wound therapy according to the invention in conjunction with a stationary suction source.

FIG. 1 shows an embodiment of a system (10) for suction wound therapy. The components include a wound dressing subsystem (12), a suction tube (14), a waste collection canister (16), a flow monitor instrument (18) and a wall suction regulator (20) of a stationary suction source.

The Wound Dressing

The typical wound dressing (12) includes a wound cover (22) and wound packing material (24), and may include a special wound contact layer (26). It will have a suction tube (14) running under the edge of the primary cover or through the cover, or will terminate outside of the cover and communicate with a nozzle or slot in the cover. There is a wide variety of each of these components. The wound dressing (12) shown in the drawings and described herein uses presently preferred components, but the invention is not intended to be limited to these components.

The primary wound cover (22) is preferably an airtight wound cover that is vapor permeable. It is preferred to use a thin film transparent commercial bandage, such as medical grade Tegaderm™ manufactured by 3M, that is impermeable to liquids but permeable to water vapor and oxygen. The term "airtight" means that the material is sufficiently occlusive to resist airflow through the cover to maintain suction under the cover while suction is being applied. There are many other thin-film commercial bandages that have similar properties. Highly impermeable materials could also be used. However, since it is beneficial in wound therapy to allow water vapor to escape and oxygen to migrate into the wound, semi-permeable covers of film material such as Tegaderm™ are preferred. In some instances, the primary cover could also be a rigid or semi-rigid enclosure placed over the wound. The primary wound cover is generally sealed to the skin surrounding the wound with an adhesive (not shown) incorporated in the cover, and gap filler paste (not shown) may be used where needed.

Before the primary cover (22) is applied, the wound is generally packed with a wound packing (24). Simple gauze or foam pads can be used, or other materials commercially sold as wound packings. The presently preferred wound packing, however, is polyester fibers or comparable resilient fibers in a corrugated layer pattern configured to form a resilient compressible structure, as described in U.S. patent application Ser. No. 10/981,119, commonly assigned with this application. The wound packing (24) may also be attached to a wound contact layer (26). The presently preferred wound contact layer (26) has a special construction that provides a wound contact surface, with depressions formed into the surface, to work in conjunction with the suction to encourage more rapid tissue regeneration, as described in U.S. application Ser. No. 10/982,346, commonly assigned with this application. The contact surface is configured such that voids formed by the depressions remain above the wound surface in the presence of moisture, compressive forces and suction, encouraging local tissue deflection.

The wound dressing includes a suction tube (14) attached to the wound cover. The dressing may have other tubes (28, in FIG. 2) for medication supply or wound flushing. The tube(s) may pass under the edge of the cover or through it, but a presently preferred arrangement uses a tube attachment patch (30) to allow the suction tube to be terminated outside of the primary cover and reduce the risk of breaking the adhesive seal to the skin, as described in U.S. application Ser. No. 11/181,128, commonly assigned with this application.

Figure 2:
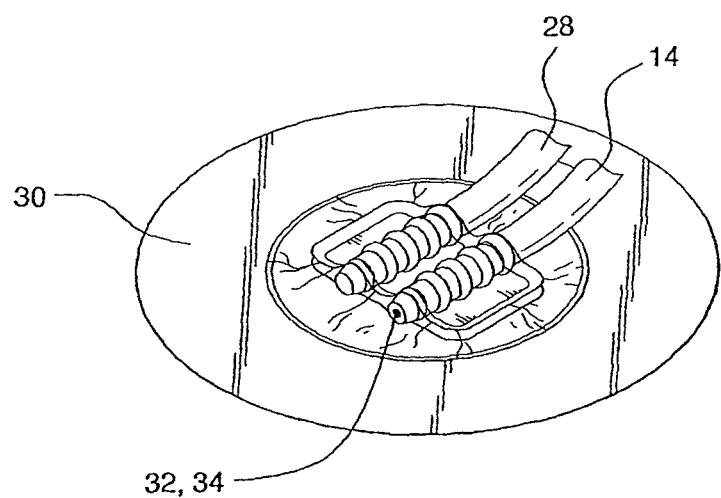
FIG. 2 is a view of a suction tube attachment device showing an air vent in the suction tube to create a controlled reference airflow rate to the suction source.

As shown in FIG. 2, the distal end of the suction tube (14) in this embodiment has a vent hole (32) that is sealed with a porous plug (34) that provides a controlled leak, or reference airflow, for the airflow monitoring devices described hereafter. It is preferable to locate the vent (32, 34) as close to the wound cover as possible. Having the tube attachment outside of the primary cover allows the use of this controlled leak reference airflow without drying out of the wound, as might occur if the vent were under the cover near the wound. While, it is feasible to place the controlled leak in the actual wound space, consideration would need to be given to avoid excessive drying of the wound tissue due to the introduced airflow. In addition, it is possible with the type of tube attachment patch (30) shown in FIG. 2 and described in U.S. application Ser. No. 11/181,128 to provide the vent as an aperture in the patch (30).

The reference airflow rate from the calibrated vent is used for monitoring system operation. The controlled leak rate should be low to maintain a proper suction at the wound site and a moist healing environment. Preferably the reference airflow is in the range of 50-300 cubic centimeters per minute. This flow is low enough to minimize drying and does not significantly alter the suction applied at the wound. Additionally, the flow is low enough to minimize the use of battery power where a portable pump is used as the suction source. A flow of this magnitude is readily obtained by providing a vent hole (32) in the suction tube that is sealed sterile with a porous plug (34), as described above. A suitable seal material is a porous plastic manufactured by Porex from sintered high density polyethylene. Such porous materials are routinely employed to admit air into medical fluid lines at a suitable flow while maintaining an efficient sterile filtration barrier against microbes.

The wound therapist applies the wound dressing (12) to the patient and attaches the system to suction. The therapist remedies leaks in the dressing by smoothing out creases or wrinkles in the wound cover and addressing gaps due to folds in the patient's anatomy. It has at times been useful to address specific areas of difficult anatomy by using a gap filling paste, as is common in ostomy care, such as Coloplast®. The airflow monitoring instruments described hereafter facilitate the initial dressing set up process by providing active feedback to the therapist on the integrity of the seal around the wound cover and tubes.

The Waste Collector

Figure 3:
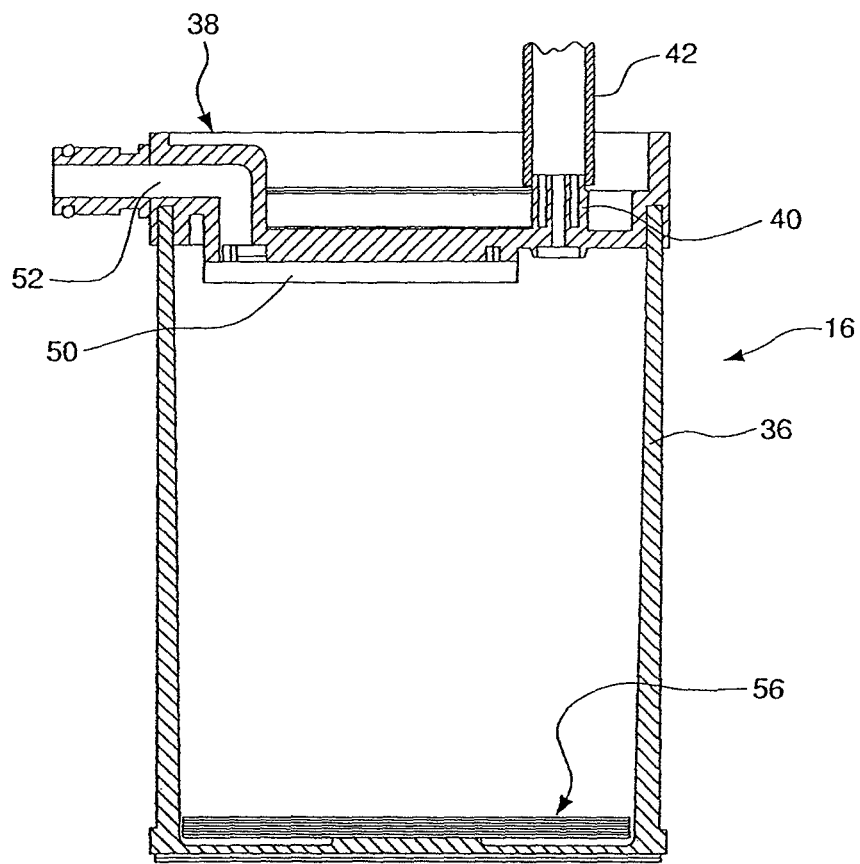
FIG. 3 is a cross section view of waste collection canister showing the shut off membrane and gel agents.

Since a primary function of suction therapy is to drain liquids from the wound, the devices normally include a waste collector (16) for collecting fluids aspirated from the wound. As shown in FIG. 3, the collector (16) is preferably an upright plastic canister (36) that may have fill level markings on the outside of the canister. The canister is preferably a disposable, single-use device. The canister has a lid (38) incorporating a fitting (40) passing through the lid for the attachment of an inlet tube (42). The inlet tube (42) may be an end of the suction tube (14) leading from the wound, or be a short section of tube that terminates with a connector fitting (44) for mating with a matching connector (46) on the end of the suction tube (14).

Airflow and any blood or other fluid aspirated from the wound passes through the fitting (40) in the lid and into the canister (36). The liquid is retained in the canister, while the air rises and is drawn through a hydrophobic membrane (50) sealed to the inside of the lid. The membrane (50) acts as a bacteria filter and as a shut off mechanism to prevent the canister from overflowing and to prevent contamination from flowing out of the container toward the suction source.

The lid defines an air channel from the outlet port (52) to another connector (54) for connecting the canister to a portable pump or to a tube running to a stationary wall suction system. The second connector (54), however, is preferably a proprietary (non-standard) connector that will not connect directly to the standard appliance fitting of a stationary suction system. This is to prevent anyone from mistakenly connecting directly to the suction system without the flow monitoring instrument and pressure release features described hereafter, with the attendant risk of applying too great a suction to the wound. The mating receptacle in the portable pump configuration described hereafter is configured to receive the proprietary connector. The connector (54) includes a sealing element such as an O-ring seal. This arrangement provides that a fresh O-ring is preferably used with each disposable canister, as contrasted with other pump connectors where the sealing element is in the pump and will ultimately wear out and cause the system to fail because of leakage.

The air passage through the canister thus forms a part of a suction conduit between the wound and the suction source. In the system presently preferred and described herein, the canister (36) is prevented from overfilling by the hydrophobic membrane (50). If the canister (36) is allowed to fill high enough for the contents to contact the membrane, the membrane occludes and blocks airflow from passing through the canister. This blockage prevents suctioning more waste from the wound, and as described hereafter, the blockage of reference airflow is detected as an indication of an abnormal operating condition.

Preferably the liquid waste sucked from the wound is turned into a gel for ease of disposal and to prevent spilling or splashing. Although the gelling agent could be provided in porous bags, it is preferred to use disks (56) of laminated fiber sheets containing a gelling agent, such as provided by Gelok International. The disks (56) are cut to fit inside of the jar and stacked on top of each other. The stacked disks cause the liquid to turn to a level surface gel in the canister.

The system may also include a filter/drier unit (21) disposed between the waste collection canister and the wound flow monitor (19). The filter element provides additional protection against contaminated particles entering the suction source, and the drier removes moisture from the air that may effect the calibration of the flow monitoring instrument.

Use of Controlled Reference Airflow to Indicate Normal Operation

While prior art suction dressing systems either do not monitor system operation at all, or do so less than optimally by trying to sense pressures directly, the system described herein uses a reference airflow, as may be provided by the air vent (32) described above, to indicate when the system is in normal operation, and also to detect deviation from the reference airflow as an indication of abnormal operation. Higher airflow than the reference flow indicates leakage, while lower airflow indicates blockage.

The range of flows suitable for reference flow are bound by the permeability of the wound cover on the lower end and suction limits on the upper end. When the wound cover is a semi permeable material, there will be a natural low level background airflow from air molecules passing through the cover. This permeation airflow could serve as the reference flow if the flow monitoring instrument were very sensitive. However, the permeation flow is usually too low and too erratic to be a good reference. The area of the cover and the possibility of it being obstructed by drapes and fluid from the wound can cause the permeation flow to be erratic. Thus, the vent provides a larger and more stable flow rate that masks variation in the permeation flow and provides a good reference. For example, Tegaderm™ bandage will allow a diffusion of water on the order of 800 grams/square meter/day, which correlates to a flow rate of about 0.5 cc/min over a square meter. Typical wound cover area would be less than a tenth of a square meter, so in approximate terms, the semi permeable material contributes 0.05 cc/min, or less than 0.1% of a reference flow of 50 cc/min. Thus, any variation in the background permeation flow is masked by the larger reference flow.

The indicator sub-system is embodied in two devices as depicted and described below; a wound monitor flow instrument for use with a stationary suction source and a portable pump with a flow sensing system. Other types of flow indicating devices, such as target meters or hot wire anemometers could also be used.

The Flow Monitor

In the wound suction system of FIG. 1, the flow rate monitor is a float meter (19) that includes a suction conduit (58) between the waste collection canister (16) and a stationary suction source (20). One end of the conduit includes a mating connector (60) to the proprietary connector (54) of the canister. The flow monitor (18) is preferably located at the other end of the conduit (58) and attaches directly to an appliance connection fitting (64) associated with an adjustable suction regulator (20) as commonly found on stationary suction systems.

The float meter (19) is designed to provide a visual indication of the flow rate through the system. Once the flow rate stabilizes at the controlled reference airflow following initial application, the maintenance of this visual indication of reference flow is an indication of normal operation free of leaks or blockage, and hence an acceptable level of suction at the wound cover. Deviation to a higher airflow indicates leakage, and drop to lower or no airflow indicates blockage in the collection circuit.

Figure 4:
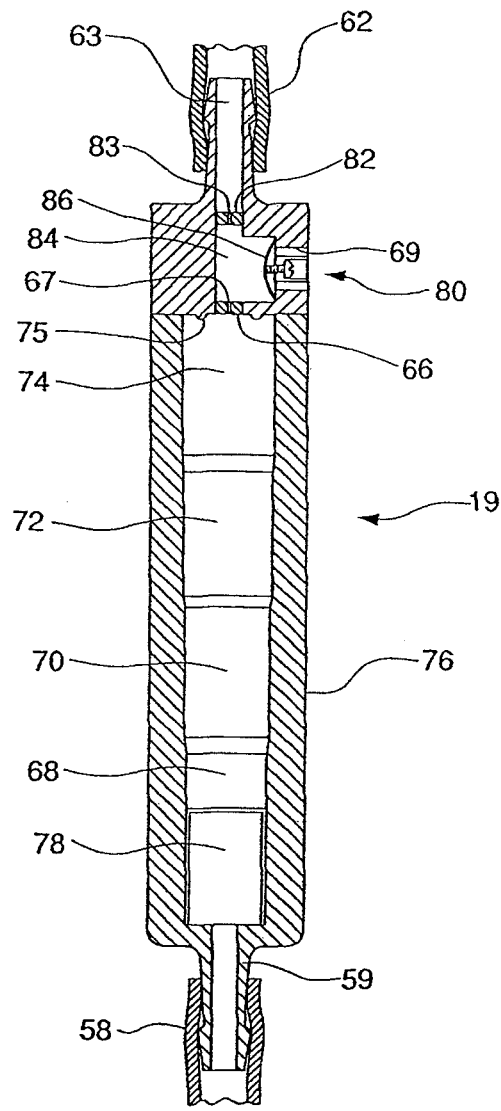
FIG. 4 is a cross-section view of the wound monitor airflow indicator.

FIG. 4 is a cross section of the float meter (19). A standard connector (63) on the top end of the indicator attaches to a short conduit (62) connectable to the appliance fitting (64) of the adjustable suction regulator (20). At the bottom end of the flow indicator a standard connector (59) is attached to the suction conduit (58). It is typical to use suction in the range of 25-200 mm Hg in wound therapy. The flow indicator incorporates a flow restrictor (66) having an orifice (67) that is calibrated to restrict suction airflow to be less than 20 liters per minute when a controlled level of suction of 100 mm Hg is applied by the suction regulator (20).

As shown in FIG. 4, the flow indicator has progressive sections (68, 70, 72, 74) with different inside diameters, having the narrowest section (68) at the bottom and progressively larger diameters in the three additional sections (70, 72, 74) progressing to the top. The outside barrel (76) of the clear tube has graduated markings (not shown) to indicate airflow rates. A float (78) serves as an indicator of flow through the system. When there is no airflow, the float will rest in the lowest section (68). This area is color coded red to indicate a blockage condition, such as a full canister or any occlusion in the fluid path. When the flow into the meter is low, preferably between about 50 cubic centimeters per minute to 300 cubic centimeters per minute, the clearance between the float and the bottom section of the indicator is such that the flow around the float will cause the float to rise into the next section (70). Thus, normal reference airflow will cause the float to rise a discernable amount into the next section. This area of normal operation is color coded green, indicating an acceptable condition.

The mass of the float works in cooperation with the clearance between the outside of the float and the inside of the tube. The float responds to airflow rate and fluid density and will rise to a level where the dynamic forces are in equilibrium. Typical flow indicators for other applications have continuously increasing inner diameters. Slight changes in flow rate cause the float to chatter up and down around a height indicative of the flow rate. The use of discrete sections of uniform diameters, but increasing in progression, as the four sections (68, 70, 72, 74) in this indicator reduces the chatter and causes the float to move upward in stages. These stages are selected for discrete flows that provide key reference information regarding the suction applied to the wound.

If flow through the system increases beyond an acceptable level due to a leak in the wound dressing, the clearance around the float in the normal position may no longer be adequate to allow the float to remain in this position, and the increased flow will lift the float to a higher section in the indicator where the internal diameter is stepped up. Graduated labeling (not shown) on the outside of the indicator provides a visual indication of a moderate leak condition. Additional stepped up diameter sections are provided to indicate higher leak conditions. The stepped up diameters require a significant change in flow before the float will jump from one position to a higher one. This eliminates the jumpiness that would be encountered with a continuous taper inner diameter as common in flow meters for other applications. The stepped diameter sections reduce user interpretation, thus enhancing ease of use and safety.

The wound monitor instrument also incorporates a safety valve (80) that limits maximum suction to guard against the accidental application of excessively high levels of suction. It is typical to use suction in the range of 25-200 mm Hg for wound drainage and therapy. Consequently, the suction limiting feature may be set to limit the suction to approximately 200 mm Hg. A suction pressure relief chamber (84) is formed between the first flow restrictor (66) and a second flow restrictor (82) having an orifice (83) the same size as the first restrictor. A resilient valve mechanism (86) in the relief chamber serves as a release against the application of high levels of suction. The valve mechanism is spring loaded to a predetermined suction setting, such as 200 mm Hg. If the suction pressure in the relief chamber exceeds the predetermined setting, the valve mechanism will open and allow vent air to be drawn from a relief port (69) into the metering orifice to prevent excess suction from being applied to the patient.

Protrusions (75) may be provided on the top underside of the interior of the float meter adjacent the first flow restriction orifice to prevent the float from completely blocking the orifice entry to the pressure relief chamber, thus allowing air passage even if a major leak occurs. This allows some suction to communicate through the system even at high airflow rates. Alternatively, the protrusions could be located on the top surface of the float.

The wound flow monitor instrument is also protected from sources of potential contamination in the form of particulate matter, aerosols and humidity by an air filter/dryer (21) located in the conduit between the instrument and the canister. The filter/dryer unit includes a particle filter for removing airborne dust as may be encountered when the wound monitor is disconnected from the collection canister for periodic changeover. It is also anticipated that a desiccant or other means of humidity control can be placed in the filter/dryer unit as required.

While this system has been described in the context of a hospital wall suction system, it can also be used with suction pumps. Some medical buildings may use electrical power pumps to provide suction for wound therapy. These can be moved, since they only restriction is the location of electrical outlets and the length of the power cord, but they are not truly portable. A system using portable battery powered pump is described below.

Portable Pump

Figure 5:
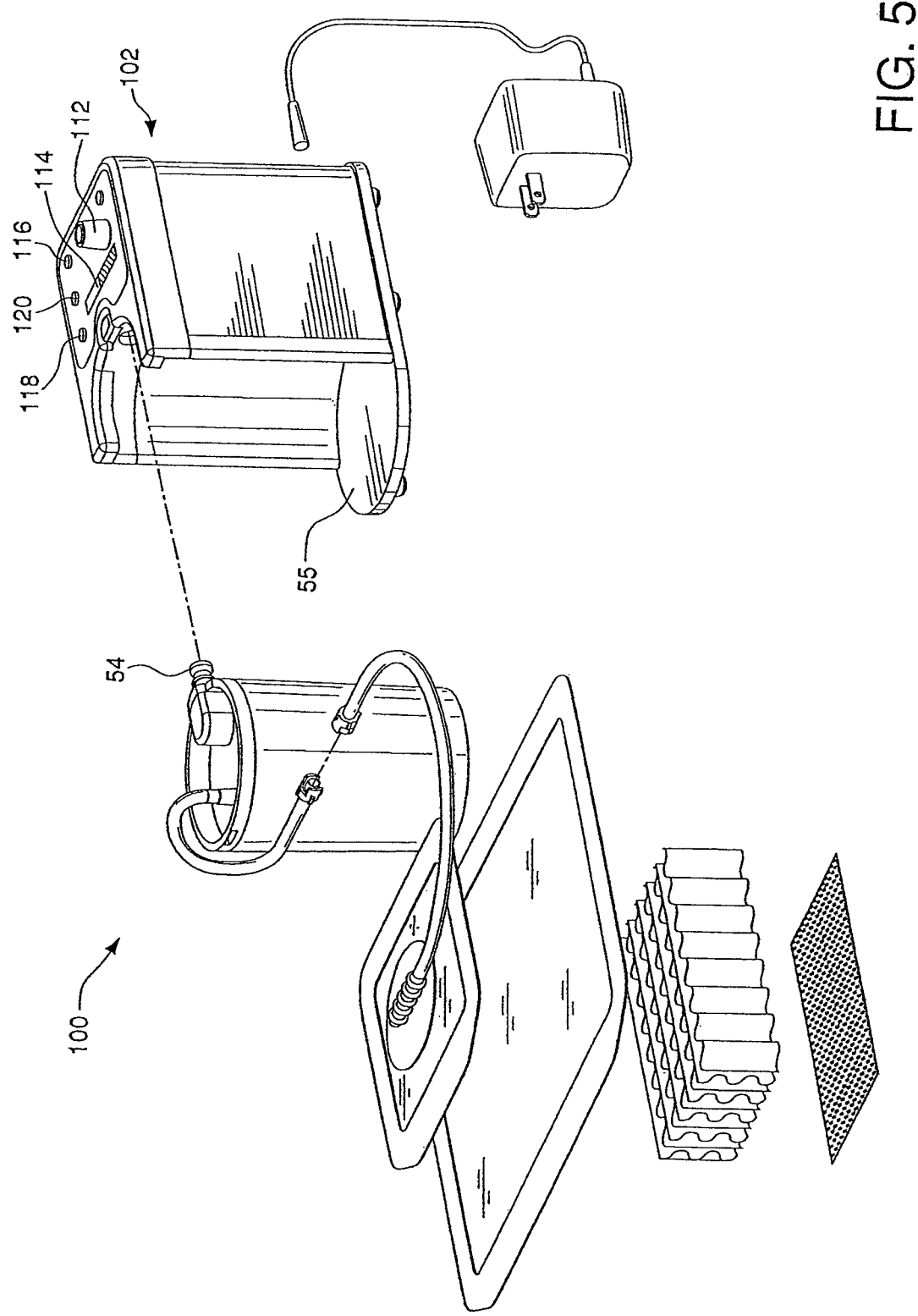
FIG. 5 is an exploded prospective view of a preferred embodiment of a system for suction wound therapy according to the invention in a portable pump configuration.

As shown in FIG. 5, a portable pump embodiment (100) uses the same wound dressing subassembly and waste collection canister as described above, but employs a portable suction pump unit (102) instead of a stationary suction source. The portable pump embodiment is configured to provide controlled levels of suction to the wound, and has a flow rate monitor to indicate abnormal operation conditions in a manner analogous to that described for the stationary embodiment. The pump operates with low voltage DC and has an onboard power source. The pump will run on wall power with a suitable power converter, which may be combined with the battery charger to charge the battery during use. The pump is turned ON using the control dial (112) on the pump housing.

Figure 6:
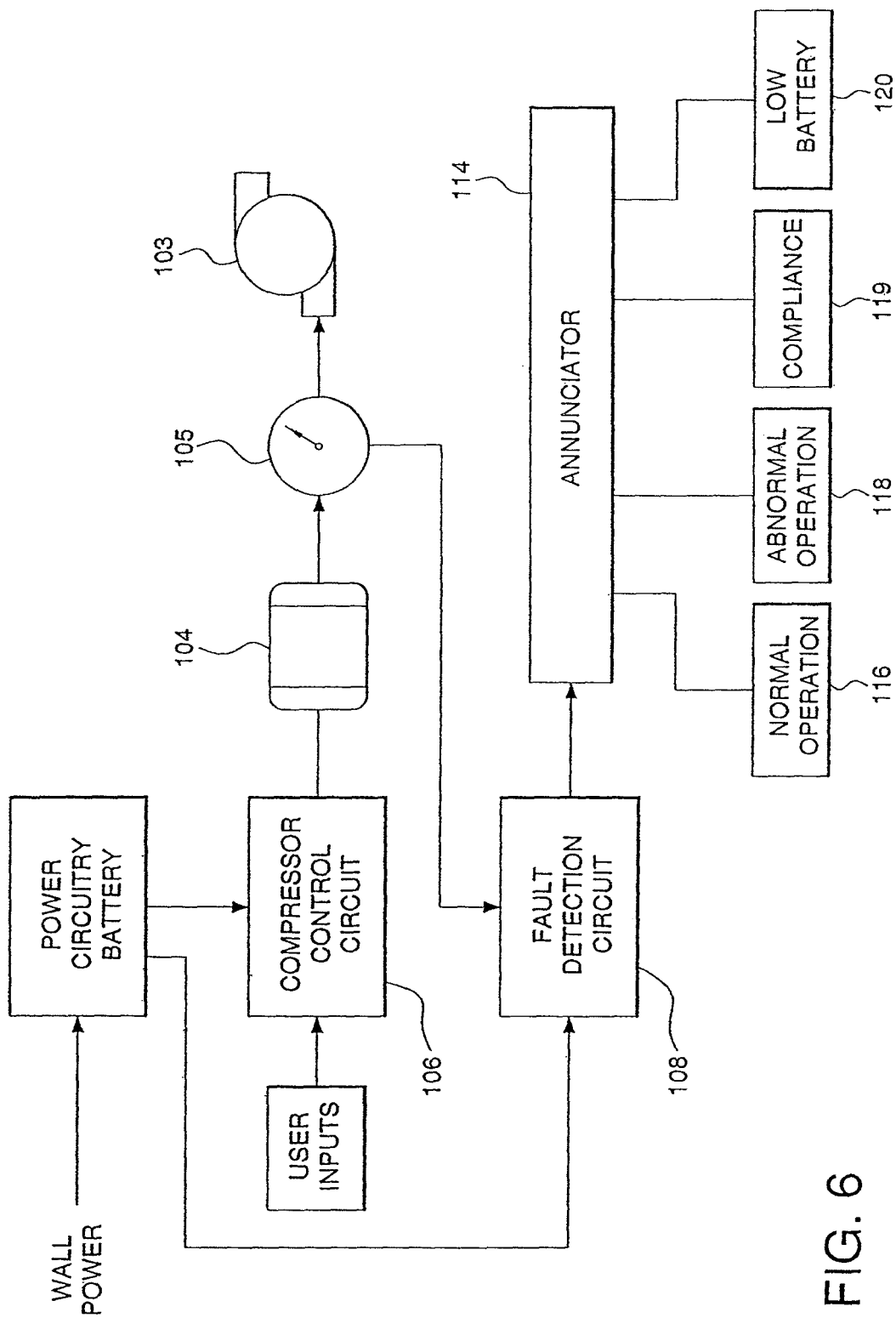
FIG. 6 is a schematic diagram of a flow monitor system of a positive displacement pump embodiment measuring motor speed as a surrogate of airflow.

When the portable pump is a positive displacement pump, it is possible to monitor pump rpm as a surrogate for airflow rate. As shown in the schematic diagram of FIG. 6, the portable pump embodiment includes a positive displacement air pump (103), a variable speed D.C. motor (104), a tachometer (105), a compressor control (106) and a fault detection/alarm system (108). The positive displacement pump (103) is preferably a diaphragm style pump with inlet and outlet check valves. The diaphragm pump includes a crankshaft style input that is operationally connected to the shaft of the variable speed motor. Other positive displacement pumps may be used, such as peristaltic, piston, syringe or rocking piston pumps.

The variable speed motor (104) is preferably a DC brushless motor, however other styles of DC motors are acceptable, as well as AC motors that can be equipped with variable outputs. It is preferable to have a motor that is equipped with some form of a tachometer (105) to indicate shaft rpm as the input to the pump. For example, Hall sensors are commonly employed on DC brushless motors, as well as encoders, to indicate rpm. It is also possible to sense back EMF in brush versions of DC motors to determine motor shaft rotation speed. In an AC pump, an oscillating bar with a magnet mounted to an end is excited by an AC coil, thus driving a diaphragm. Pump input in this case is a count of the oscillations delivered by said coil. Each of these and other forms of pump or motor speed sensors is included in the generic term tachometer, and can be used as the flow rate monitoring instrument with a positive displacement pump.

The compressor control (106) is typically a pressure transducer and a control circuit that permits the user to select a pressure setting, and the circuit will function to maintain the suction pressure at the input of the pump at a level consistent with the selection. Such control circuits are commonly employed in industrial applications as well as in hospital central suction systems. Compressor control circuits are adjusted to maintain suction or pressure levels in a specified range. This range is selected to provide a reasonably stable suction level while minimizing on-off cycling of the motor. In this portable pump embodiment, a range of approximately 10 mm Hg is preferred for patient comfort and to minimize noise. For example, at a setting of 100 mm Hg, the compressor control will nominally maintain a suction pressure at the inlet of the pump in the range of 95 to 105 mm Hg.

The fault detection system (108) is a circuit that is adapted to monitor the flow of air through the collection circuit coupled with an annunciator to provide audible and visual indication of status of operation. This fault detection system is a separate circuit that is independent of the compressor control. In the preferred embodiment, motor or pump revolutions are counted as an indication of air volume that has passed through the positive displacement pump. A discrimination algorithm takes the count of motor revolutions and determines a flow rate. This flow rate is compared to the known reference flow rate to determine fault conditions. A flow rate that is less than the reference flow of 50-300 cc/minute is indicated as abnormal operation on the annunciator as an occlusion in the circuit, most commonly a full canister. A flow rate that is comparable to the reference flow rate produces an annunciator indication of normal operation. Flow rates that are higher than the reference flow rate will produce abnormal annunciator indications that the circuit is leaking to alert the caregiver to address the seal of the wound cover. If the caregiver is able to correct the leaking dressing the annunciator will indicate normal operation. Thus, the fault detection system of the portable pump is analogous to that of the wound monitor flow instrument.

It is sometimes desirable, to benefit the healing process, to provide suction in an intermittent fashion. Prior processes involve allowing the system to vent to atmospheric pressure for a period of time to allow for reperfusion of tissue. Allowing the system to completely vent to atmosphere results in the complete loss of suction on the dressing system and any benefit that suction could play in maintaining an air tight seal around the wound. The present invention solves this problem by varying the suction between two distinct levels; a first level and a second level of 20-25 mm Hg. The first and higher level is employed to apply the beneficial effects of suction. The second and reduced level is below capillary bed pressure, so reperfusion of tissues will occur in this lower stage, while maintaining at least some level of suction to aid in keeping the dressing in place and to maintain the reference airflow to prevent reflux and clotting in the lines. With this type of intermittent pump operation, the reference airflow should be selected such that it is maintained even at the reduced level, or else the alarms associated with low airflow should be disarmed during reduced suction intervals as well as the ramp-up and ramp-down intervals.

The annunciator may be in the form of a bar meter (114) color coded and graduated to provide a visual indication that the flow through the pump is within a range required to maintain the reference airflow when the system is in normal operation; and conversely indicate that the pump is running faster than required to maintain the reference airflow, indicating air leakage in the system, or is running slower than required to maintain the reference airflow, indicating air blockage in the system. The pump may also have warning or caution lights (116, 118, 120) indicating pump operating parameters, or other parameters such as low battery charge. The pump may also provide an audible indication of abnormal operation, such as a beeper tone.

The pump is connected to the proprietary fitting (54) of the waste canister, and may have a conforming docking station (55) to support the canister. The prescribed pressure setting is selected by a dial (112), which preferably allows set-point choices of 25, 50, 75, 100, 125, 150, 175, or 200 mm Hg. Electronic controls provide the ability to enable numerous combinations of fault indications, both visual and audible.

Target Meter Alternative

Figure 7:
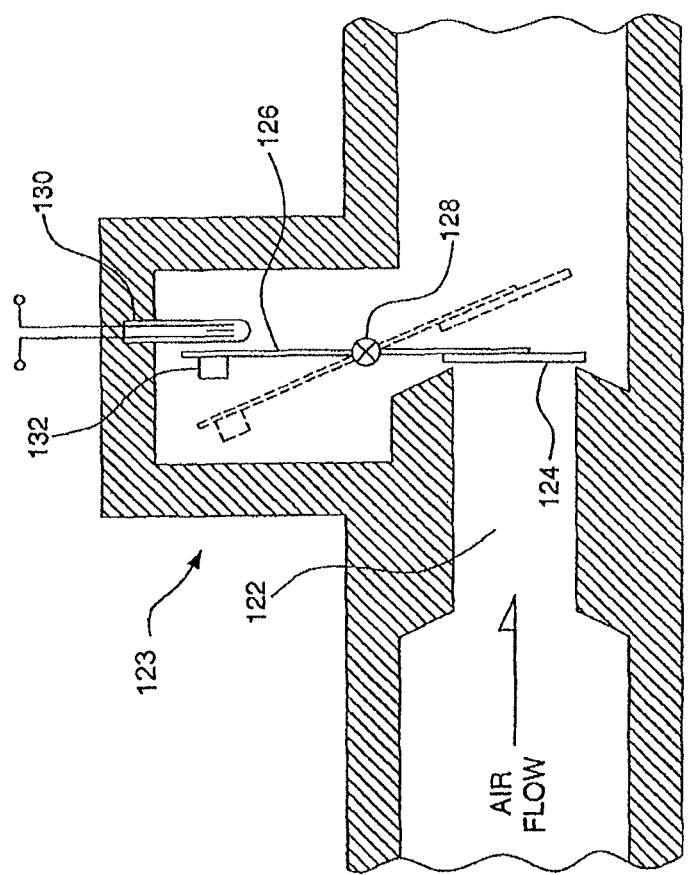
FIG. 7 is a schematic view of a target meter flow indicator alternative.

There are other devices for determining the flow through the system that could be employed as leak detection devices in a wound dressing system operating with a reference airflow. These devices measure airflow directly, and thus can be used with non positive displacement pumps and wall vacuum sources as well as with positive displacement pumps. As shown in FIG. 7, a target meter (123) is a reliable device for flow detection that is insensitive to changes in pressure. The target meter (123) employs an inlet orifice (122) and a target (124) typically placed in close proximity to the orifice. The target is attached to a shaft (126) and pivots on points (128) or an armature. A light torsion spring (not shown) may be used to keep the target in close proximity to the orifice. The extension of the shaft is placed outside of the flow path. As airflow enters the orifice, the target is forced away from the orifice. A proximity sensor, such as a reed switch (130) is so placed as to detect the positions of a magnet (132) on the end of the shaft extension and thus the presence or absence of flow in the circuit as well as measuring flow rate. A target meter could be placed between the waste collection canister and the pump or at the outlet of the pump, or between the waste collection canister and a stationary suction source to provide analogous flow rate information as previously described.

Flow Measurement Alternatives

Other flow detection devices that could be used alone or in conjunction with a suction source include a hot wire anemometer that determines flow as a function of the cooling of a wire in a flowing air stream, a rotameter with an optical detector that senses the position of a float, a turbine meter that rotates when flow is applied. These flow detection systems are generally insensitive to changes in pressure. A hot wire anemometer could be placed between the waste collection canister and the pump or at the inlet of the pump, or between the waste collector and or a stationary suction source. These alternative flow sensors allow the use of other styles of pumps that are not positive displacement, such as vane pumps and scroll pumps. Almost any flow instrument could be used, including, for example, differential pressure (DP) cells that provide an indirect measure of flow rate.

When any fault condition is determined within the system, the pump will continue to run, delivering a sub-optimal level of suction, until the condition is corrected or the user powers the system off, since a sub-optimum level of suction applied to the wound is preferable to no suction at all.

The pump may also have an onboard compliance monitor. This alerts the caregiver to deviations from the normal application of suction to the wound. The compliance monitor may compute the number of hours that clinically useful suction has been applied to the wound as determined by the relative flow through the system. Medical experience has shown that suction should be applied for at least 22 of any 24 continuous hours for optimum efficiency. This readout can be presented a number of ways to show the number or percentage of compliant hours of suction therapy. A percentage can be reduced to a dimensionless parameter indicating acceptable or unacceptable compliance.

Therapeutic Fluid Delivery and Reference Flow

Figure 8:
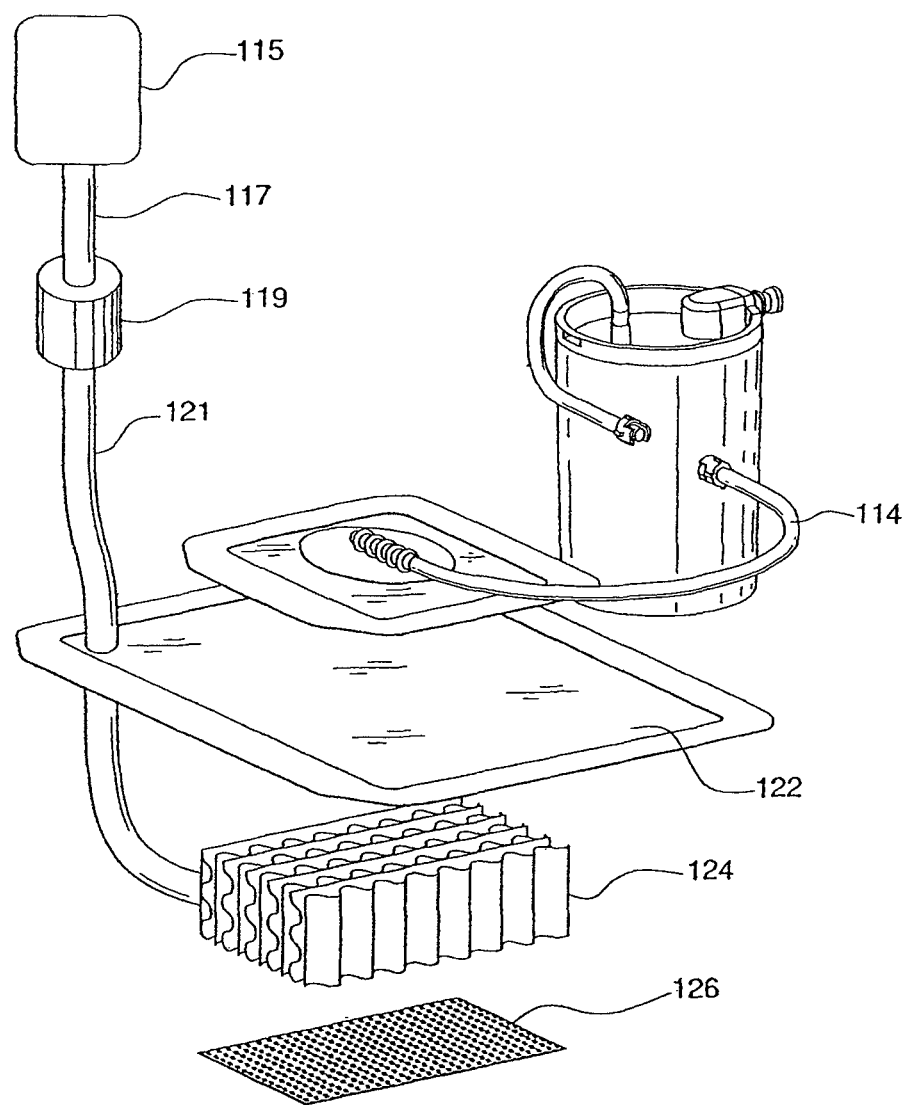
FIG. 8 is an exploded prospective view of a portion of an alternative embodiment of a system for suction wound therapy according to the invention using a therapeutic fluid delivery to the wound.

In the embodiments described above, the reference flow for discerning between normal and abnormal operation has been ambient air supplied to the suction conduit through a vent. A reference airflow could be provided, however, in the form of a therapeutic mixture, such as oxygen enriched air, nitric oxide, heated humidified air or an aerosol containing medication droplets or particles. Such a configuration is shown in FIG. 8. A source of therapeutic mixture (115), such as an oxygen regulator or a nebulizer, is connected to a conduit (117) leading to the wound. The mixture is conveyed through the conduit under or through the wound cover (122) and released into the wound packing (124) adjacent the wound contact material (126). Part of this mixture will be absorbed, but enough could be returned through the suction conduit (114) to provide a reference airflow when the flow has settled into equilibrium.

While the airflow monitor could be associated with a portable pump or in front of the appliance fitting of a suction regulator, as described above, an airflow monitor (119) could be provided between the therapeutic mixture source (115) and the wound cover (122). Since the part of the conduit beneath the cover would be contaminated in use, a detachable disposable tube (121) would be used for the section of conduit from the monitor to the wound packing. Thus, the invention can provide for the maintenance of suction therapy on a wound as well as the ability to monitor the application and removal of therapeutic substances to the wound.

Although the invention has been described and illustrated with respect to several embodiments described above, it should be understood the invention may be embodied in other forms without departing from its scope or attributes. Hence, the scope of the invention should be derived from the claims that follow, recognizing that the claim language may literally encompass structure not specifically described.

What is claimed is:

1. A system for applying suction to a wound, comprising:
   a portable positive displacement pump for providing suction to a conduit operatively associated with the wound to communicate suction to the wound, the pump being capable of operation at variable speed;
   a vent in fluid communication with the conduit to provide a reference airflow into the conduit when the system is in operation, such that a loss of suction at the wound is indicated by deviation from the reference airflow;
   a flow rate monitor to monitor airflow through the conduit and to indicate reference airflow and deviation above and below the reference airflow; and
   a pressure transducer for detecting pressure at the pump, wherein the pump speed is controlled to maintain the pressure sensed by the transducer based on a pressure setting;
   wherein the airflow is determined by counting pump revolutions over a period of time.

* * * * *